(12) United States Patent
Bettini et al.

(10) Patent No.: US 9,717,693 B2
(45) Date of Patent: Aug. 1, 2017

(54) COMPOSITIONS OF MICROPARTICLES AND GRANULES FOR ORAL CONTROLLED RELEASE OF SUBSTANCES FOR VETERINARY USE

(75) Inventors: Ruggero Bettini, Torrile (IT); Lauro Arduini, Cavriago (IT); Francesca Bertolini, Collecchio (IT); Claudia Camellini, Cavriago (IT)

(73) Assignee: KEMIN INDUSTRIES, INC., Des Moines, IA (US)

( * ) Notice: Subject to any disclaimer, the term of this patent is extended or adjusted under 35 U.S.C. 154(b) by 1359 days.

(21) Appl. No.: 12/309,828

(22) PCT Filed: Jul. 31, 2007

(86) PCT No.: PCT/EP2007/057861
§ 371 (c)(1),
(2), (4) Date: Jan. 19, 2010

(87) PCT Pub. No.: WO2008/015203
PCT Pub. Date: Feb. 7, 2008

(65) Prior Publication Data
US 2010/0112075 A1 May 6, 2010

(30) Foreign Application Priority Data
Aug. 4, 2006 (IT) .............................. MI2006A1583

(51) Int. Cl.
| | | |
|---|---|---|
| *A61K 9/20* | (2006.01) | |
| *A61K 9/50* | (2006.01) | |
| *A61K 9/00* | (2006.01) | |
| *A23K 40/35* | (2016.01) | |
| *A23K 20/142* | (2016.01) | |
| *A23K 20/10* | (2016.01) | |
| *A23K 20/24* | (2016.01) | |
| *A23K 20/28* | (2016.01) | |

(52) U.S. Cl.
CPC ............ *A61K 9/5015* (2013.01); *A23K 20/10* (2016.05); *A23K 20/142* (2016.05); *A23K 20/24* (2016.05); *A23K 20/28* (2016.05); *A23K 40/35* (2016.05); *A61K 9/0056* (2013.01); *A61K 9/5073* (2013.01)

(58) Field of Classification Search
CPC .......... A61K 9/141; A61K 9/148; A61K 9/16; A61K 9/1605; A61K 9/1607; A61K 9/1635; A61K 9/167; A61K 9/1682; A61K 9/1694
USPC ................................................ 424/464–489
See application file for complete search history.

(56) References Cited

U.S. PATENT DOCUMENTS

| | | |
|---|---|---|
| 3,541,204 A | 11/1970 | Sibbald et al. |
| 4,533,557 A | 8/1985 | Maruyama et al. |
| 4,713,245 A | 12/1987 | Ando et al. |
| 4,832,967 A | 5/1989 | Autant et al. |
| 4,876,097 A | 10/1989 | Autant et al. |
| 5,077,053 A * | 12/1991 | Kuncewitch ............. A23G 3/20 424/441 |
| 5,190,775 A | 3/1993 | Klose |
| 5,496,571 A | 3/1996 | Blagdon et al. |
| 5,912,017 A | 6/1999 | Mathiowitz et al. |
| 5,928,687 A | 7/1999 | Meade et al. |
| 5,958,458 A * | 9/1999 | Norling ................ A61K 9/0007 424/466 |
| 6,013,286 A | 1/2000 | Klose |
| 2004/0086564 A1 | 5/2004 | Richardson et al. |
| 2005/0019413 A1 | 1/2005 | Cavassini et al. |
| 2006/0067984 A1 * | 3/2006 | Cavassini ............ A61K 9/1611 424/438 |

FOREIGN PATENT DOCUMENTS

| | | |
|---|---|---|
| BR | 8502688 | 2/1986 |
| CA | 2256256 | 6/2000 |
| EP | 0467401 | 1/1992 |
| EP | 0477135 | 3/1992 |

(Continued)

OTHER PUBLICATIONS

Soybean Oil entry (en.wikipedia.org/wiki/Soyben_oil) Feb. 9, 2015.*
Palmi Oil entry (en.wikipedia.org/wiki/Pail_oil) Feb. 9, 2015.*
Soybean oil entry (en.wikipedia.org/wiki/soybean_oil).*
Palm oil entry (en.wikipedia.org/wiki/Palm_oil).*

(Continued)

*Primary Examiner* — Micah-Paul Young
(74) *Attorney, Agent, or Firm* — Nyemaster Goode P.C.

(57) ABSTRACT

Microparticles or granules intended for use in the zootechnical field, constituted by a core which contains a substance having a pharmacological action, a food supplement or a diagnostic medium, intimately mixed or adsorbed with a hydrated silicate of magnesium, aluminum, calcium and sodium (smectite, montmorillonite or bentonite); the core is coated with a double fatty layer constituted by two fats or waxes, of which the one having the highest melting point constitutes the inner layer while the one having the lowest melting point is arranged so as to form the outer layer. The ability to control release effectively and accordingly reduce rumen degradation of active substances which contain a cationic or an anionic chemical function, such as for example choline chloride lysine hydrochloride, calcium chloride, citric acid, ascorbic acid or nicotinic acid is determined by the synergistic action of two phenomena: an interaction between the active substance and the other component of the core, and the barrier effect of the double fat layer. Taken individually, the two phenomena are unable to apply effective control over the release of the active substance.

31 Claims, 1 Drawing Sheet

(56) References Cited

FOREIGN PATENT DOCUMENTS

| | | |
|---|---|---|
| EP | 0678246 | 10/1995 |
| EP | 0 940 088 A1 * | 3/1999 |
| EP | 0940088 | 9/1999 |
| GB | WO 9608168 A1 * | 3/1996 ............ A23K 1/005 |
| WO | 96/08168 | 3/1996 |
| WO | WO 9608168 A1 * | 3/1996 |
| WO | WO9608168 A1 * | 3/1996 |
| WO | 2005/006876 | 1/2005 |
| WO | 2006/032958 | 3/2006 |
| WO | WO 2006032958 A2 * | 3/2006 |

OTHER PUBLICATIONS

J.R. Hartwell et al., "Impact of Dietary Rumen Undegradable Protein and Rumen-Protected Choline on Intake, Peripartum Liver Triacylglyceride, Plasma Metabolites and Milk Production in Transition Dairy Cows," J. Dairy Sci. (2000) 83, 2907-2917.

K.N. Deulcher et al., "Milk Choline Secretion as an Indirect Indicator of Postruminal Choline Supply," J. Dairy Sci. (1998) 81, 238-242.

F.S. Ghazy et al., "Adsorption Characteristics of Certain Antibiotics to Veegum and Activated Charcoal," Pharmazie 39 H. 12 (1984) pp. 821-823.

* cited by examiner

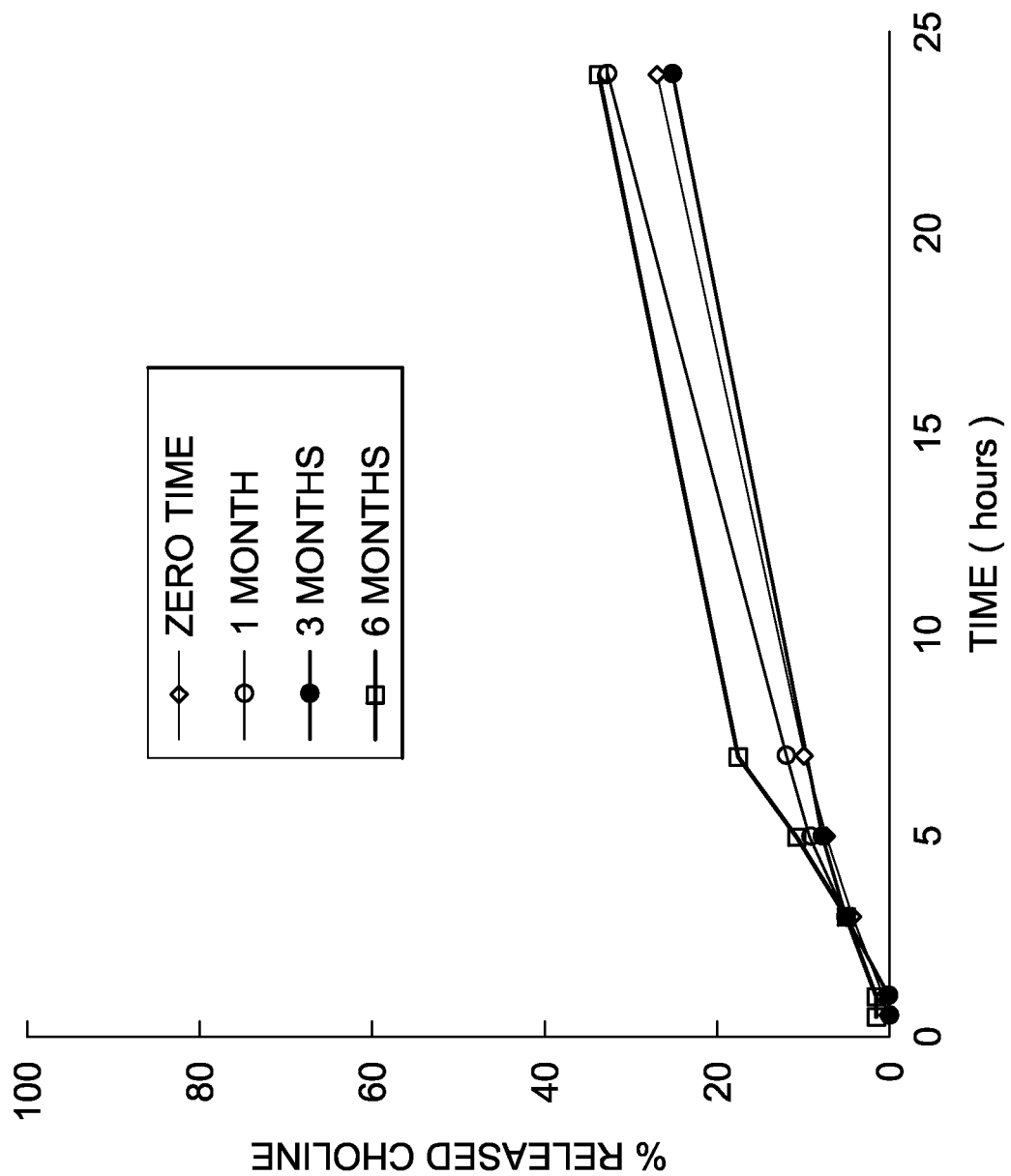

COMPOSITIONS OF MICROPARTICLES AND GRANULES FOR ORAL CONTROLLED RELEASE OF SUBSTANCES FOR VETERINARY USE

PRIORITY

This application claims benefit from International Application No. WO 2008/015203 A2, having PCT Publication No. PCT/EP2007/057861, which was filed on 31 Jul. 2007, which in turn claims priority to MI2006A001583 (Italy), filed 4 Aug. 2006, which applications are incorporated herein by reference in their respective entireties.

TECHNICAL FIELD

The present invention discloses compositions for preparing microparticles or granules intended for use in the zootechnical field, for the controlled release of one or more substances having a pharmacological action, food supplements or diagnostic media, suitable for oral administration, and the method for producing said microparticles or granules.

BACKGROUND ART

The oral administration of active substances in the zootechnical field is a problem which is not easy to solve, in particular as regards the possibility to ensure intestinal absorption of adequate doses of said substances, avoiding their massive degradation during passage through the digestive tract of the animal, especially in the case of ruminants.

The aspects of the physiology of the digestive tract of ruminants and of other so-called companion animals or productive livestock are disclosed in detail in many specialist monographs. Among these, some also review the problems linked to the oral administration of active ingredients in such animals, as well as the possible solutions in terms of formulation technology (*Development and formulation of veterinary dosage forms* 2nd Edition, G. E. Hardee, J. D. Baggot (Edts) Marcell Dekker, New York 1998; S. H. W. Wu, A. Papas, *Rumen stable delivery systems, Advanced drug delivery reviews* 28 (1997) 323-334). The active ingredients and the supplements of the animal's diet undergo, in the proximal tract of the digestive system, an enzymatic and chemical degradation before reaching the intestinal lumen, which is the site of absorption for said substances. In ruminants, this degradation is particularly substantial due to the presence, in the rumen, of a microflora which degrades effectively many of the substances which pass through the rumen. One must also consider the slowness with which said substances pass through the rumen. This causes only a small part of the active substances or food supplements to be absorbed by ruminants at the intestinal level, since almost 100% of these molecules is degraded by the microflora of the rumen. Therefore, to allow such substances to be absorbed in the intestine and apply their effectiveness, it is necessary to protect them against degradation at the rumen level. It is in fact known that for example a substance such as choline or its salts are capable of increasing milk production in bovines when they are administered directly at the post-rumen level (S. R. Haretewell et al., *J. Dairi Sci.* (2000) 83, 2097-2017 and K. N. Deulcher et al., *J. Dairi Sci.*, (1998) 81, 238-242).

U.S. Pat. No. 4,533,557, granted to Nippon Soda Ltd, discloses the composition of food supplements for ruminants in the form of granules or tablets which contain a mixture of biologically active substances, chitosan and protective materials constituted by saturated or unsaturated aliphatic monocarboxylic acids, with a chain having 14 to 22 carbon atoms. The concept behind this invention consists in using hydrophobic substances to build a matrix which is capable of slowing the penetration of biological fluids inside it and consequently of causing a slower release of the substance. The aim is therefore to extend the substance release time by reducing the amount thereof released during rumen transit. Further, the presence of chitosan should provide specific protection against the rumen environment: the pH of the fluid contained in the rumen varies between 5 and 8; chitosan is scarcely soluble in this pH range, but dissolves instead in an acid pH (<5). Therefore, the presence of this type of polymer should give greater integrity to the matrix during rumen holding.

U.S. Pat. No. 5,190,775, granted to the Balchem Corporation, discloses the composition of particles or granules for oral administration having a relative density between 0.3 and 2 g/ml, which contain a bioactive substance which is encapsulated by means of a hydrophobic coating which is constituted preferably by hydrogenated vegetable oils coated on their surface with a layer of surfactant in order to prevent its floating within the rumen. In the specific case in which the bioactive substance is choline chloride, it is adsorbed on a vegetable substrate derived from cereals.

In another patent, granted to Morgan Manufacturing Co., Inc. (U.S. Pat. No. 5,496,571), a method is disclosed for manufacturing microcapsules which are intended for oral administration and are designed to protect choline chloride against degradation caused by rumen bacteria in order to increase the production of milk in ruminants. These microcapsules contain liquid compositions of choline chloride coated with an outer layer of lipid material selected among hydrogenated and non-hydrogenated animal fats or among hydrogenated vegetable oils.

A series of other patents claims methods and compositions which entail coating a core which contains a bioactive substance by way of materials which are capable of withstanding at least partly rumen degradation and of dissolving and/or degrading in the abomasus or in the distal part of the intestine of ruminants. Among these patents, mention can be made for example of U.S. Pat. No. 4,713,245, U.S. Pat. No. 3,541,204, and U.S. Pat. No. 4,876,097.

U.S. Pat. No. 4,832,967, granted to Rhone Poulenc Santé, claims a composition for feeding ruminants which is constituted by a core which contains the bioactive substance, coated by two protective layers. The first of said coatings is a polymeric substance which is capable of forming a film which is stable at pH >5 but is capable of releasing the bioactive substance at pH <3.5. The second coating is a hydrophobic substance.

The preparation of multilayer polymeric microspheres for controlled release of drugs, fertilizers, insecticides and chemical indicators is claimed by U.S. Pat. No. 5,912,017, granted to the Massachusetts Institute of Technology.

In US Patent Publication No. 2005/0019413, Ascor Chimici S.r.l. claims a composition in the form of particles which contain choline chloride administered in a rumen-protected form. The particles are constituted by a core which consists mainly of choline chloride in the form of crystalline powder, coated by a double protective layer: externally, a continuous layer of carnauba wax and internally a continuous layer of a hydrophobic substance such as hydrogenated soybean oil. Moreover, the core can contain additional substances acting as flow modifiers (silicate, aluminosilicates, zeolites, silica, pearlite) in amounts not exceeding 8% of the weight of the core, and/or acting as binding agents which have a barrier function against moisture (stearates) in an amount equal to 7% of the weight of the core.

In a second patent application (US Patent Publication No. 2006/0067984), the same Ascor Chimici S.r.l. claims the invention of compositions in the form of pellets for controlled release of physiologically active substances for zootechnical use. These compositions comprise: i) a core constituted by the physiologically active substance and by a matrix of carnauba wax and/or microcrystalline wax; ii) a first hydrophobic coating layer, which consists of a material which belongs to the category of fats, fatty acids, hydrogenated oils, fatty acid mono- or diglycerides, fatty acid esters or long-chain alcohols (12 to 22 carbon atoms), with a melting point between 40 and 74° C.; iii) a second coating layer over the first one, which is constituted by microcrystalline waxes, paraffin waxes, vegetable waxes and synthetic waxes with a melting point between 80 and 100° C.

One of the claims further specifies that the matrix that constitutes the core can also contain hydrophobic silicates.

DISCLOSURE OF THE INVENTION

The aim of the present invention is to provide compositions in the form of microparticles or granules intended for use in the zootechnical field and/or more generally in the veterinary field which are capable of controlling, by slowing it, the release in the gastrointestinal tract of animals, particularly ruminants, of one or more substances which have a pharmacological action, food supplements or diagnostic media, said substances being characterized by the presence, within their chemical structure, of a cationic function or an anionic function or of a neutral but easily ionizable function in order to obtain a net charge. In such compositions, the substance or substances carried by the microparticles or granules are protected against the degradation that can occur in the first part of the gastrointestinal tract, in particular in the rumen, and can instead be released and absorbed in the intestine.

A specific characteristic of the method for preparing the compositions disclosed in the present invention relates to the fact that the preparation of said microparticles or granules occurs without using organic solvents.

Within this aim, an object of the present invention is to provide microparticles or granules which have technological and chemical-physical characteristics which are adapted to avoid their degradation during processes for the industrial production of pharmaceutical products or feeds (for example mixing with other ingredients, heating, application of pressure).

This aim and this and other objects, which will become more clear from the description that follows of the invention, are achieved by the system for the controlled release of one or more physiologically or pharmacologically active substances, represented by compositions in the form of microparticles or granules having a size between 0.1 and 5000 microns and intended for use in the zootechnical field and/or more generally in the veterinary field, constituted by a core which contains one or more substances having a pharmacological action, food supplements or diagnostic media, said substance or substances being characterized by the presence, within their chemical structure, of a cationic function or of an anionic function or of a function which is neutral but can be easily ionized in order to obtain a net charge, intimately mixed or adsorbed with a hydrated silicate of magnesium, aluminum, calcium and sodium (smectite, montmorillonite or bentonite), hereinafter referenced simply as silicate, which is capable of absorbing water and causing reversible swelling; said core is coated by a double fatty layer constituted by two fats or waxes, in which the one having the highest melting point constitutes the inner layer (in contact with the core) while the one having the lowest melting point is arranged so as to form the outer layer.

WAYS OF CARRYING OUT THE INVENTION

Examples of substances with a cationic function or a neutral but easily ionizable function suitable for the purpose cited above are: choline and its salts, particularly choline chloride, betaine, betaine hydrochloride, methionine hydrochloride, carnitine hydrochloride, lysine hydrochloride, thiamine hydrochloride, thiamine mononitrate, pyridoxine hydrochloride, calcium chloride, calcium sulfate, streptomycin, colistin sulfate, tiamulin fumarate, neomycin arginine, glucosamine, niacinamide and salts thereof, particularly the sulfate.

The core of the microparticles or granules according to the present invention can also be constituted by active substances characterized by the presence, within their chemical structure, of an anionic function or of a function which is neutral but can be ionized easily, such as for example but not limitatively, citric acid, malic acid, lactic acid, ascorbic acid, nicotinic acid intimately mixed or adsorbed with one or more excipients containing a cationic chemical function, selected for example but not limitatively among cationic starches, cationic derivatives of cellulose, acrylic polymers with amine groups, chitosan, clay derivatives. Such core is coated by a double layer of fat, constituted by two fats or waxes, of which the one with the highest melting point constitutes the inner layer while the one with the lowest melting point is arranged so as to form the outer layer. The ability to control release effectively is determined by the synergistic action of two phenomena: an interaction between the active substance and the excipient or excipients of the core, and the barrier effect of the double fat layer.

The controlled-release system according to the present invention is provided by preparing microparticles or granules with a method which is composed of the following steps:

preparing a mixture of powders which comprises the active ingredient or ingredients and the silicate. The amount of silicate is comprised between 20 and 80% and preferably between 30 and 70%, even more preferably between 35 and 55% of the weight of the mixture. Optionally, the mixture can also contain excipients capable of improving the formation of granules or microgranules, such as for example microcrystalline cellulose, polyvinylpyrrolidone, calcium phosphate, in an amount comprised between 2 and 20% of the weight of the mixture. Mixing can be performed with ordinary fixed- or rotating-body mixers, since the choice of the type of mixer is not particularly critical with respect to the intended result. Starting from said mixture, microgranules or granules are formed by adding water in a quantity which is sufficient to achieve agglomeration but not a cohesive mix; the amount of water that is added is comprised between 5 and 50%, more preferably between 10 and 30%, and even more preferably is 20% of the weight of the mixture of powders. The process for forming the granules or microgranules can be performed with the techniques commonly described for processes for granulation or agglomeration in the pharmaceutical field and in the food or fodder industry. Examples in this regard are described abundantly in specialist literature, such as for example in *Pharmaceutical principles of solid dosage forms*, J. T. Carstensen (Ed.)

(1993), Technomic Publishing Co., Lancaster (USA), or *Pharmaceutical Pellettization Technology* I. Ghebre-Sellassie (Ed.) (1989), Marcel Dekker, New York (USA), or *Principi di tecnologie farmaceutiche*, P. Colombo et al. (Eds.) (2004), Casa Editrice Ambrosiana, Milan (Italy), and are represented for example by the processes of extrusion-spheronization, fluid-bed granulation, rotating plate granulation, high-speed granulation, wet granulation.

In terms of use for the purposes of the present invention, the granulation methods that can be used are those that allow to use water or an aqueous solution to facilitate contact between the active ingredient or ingredients and the silicate.

As an alternative to the method described above, the powder of the silicate can be transformed into granules or microgranules by spraying it or mixing it with an aqueous solution which contains the active ingredient or ingredients. In this case, the concentration of said solution is comprised between 0.05 and 0.95 g/ml and preferably between 0.2 and 0.8 g/ml and even more preferably between 0.5 and 0.75 g/ml.

In this case also, it is optionally possible to add to the silicate excipients which are capable of improving the formation of granules or microgranules, such as for example microcrystalline cellulose, polyvinylpyrrolidone, calcium phosphate, starch, in an amount comprised between 1 and 15% of the weight of the silicate.

The amount of solution of active substance that is added is such that the amount of active ingredient is comprised between 80 and 20 parts by weight and preferably between 70 and 30 parts by weight, even more preferably between 65 and 45 parts by weight.

In this case also, the method for producing the granules can be for example extrusion-spheronization, fluid-bed granulation, rotating plate granulation, high-speed granulation, and wet granulation.

In both of the production methods described above, once the granules or microgranules have been obtained, they are dried if necessary with a drying method which uses a static or dynamic bed.

The granules thus obtained are coated with a layer of vegetable-derived fat which has a melting point comprised between 63 and 90° C. and preferably equal to 65° C. The preferred fat is constituted by mixtures of partially hydrogenated fatty acid triglycerides or by a mixture of free fatty acids, with chains having 14 to 20 carbon atoms, preferably C16 and C18. In particular, the preferred conditions provide for a content of C16 fatty acid triglycerides comprised between 10 and 30% and of C18 comprise between 65 and 90% of the total fatty acid content.

Said fat can be applied to the surface of the cores prepared as described earlier, after melting said fat, by means of a so-called fluid bed or spray congealing technique or by drum mixer coating or in any case with a coating method such as those shown for example in the monograph *Coated pharmaceutical dosage forms. Fundamentals, manufacturing techniques, biopharmaceutical aspects, test methods and raw materials*, K. H. Bauer, K. Lehmann, H. P. Hosterwald, G. Rothgang (Edts), CRC Press, Boca Raton 1998.

The coated cores thus obtained are subjected to a second coating with a vegetable fat which has a melting point comprised between 58 and 63° C. and preferably between 59 and 62° C. The fat is constituted preferably by mixtures of partially hydrogenated fatty acid triglycerides or a mixture of free fatty acids, with a chain of 14 to 20 carbon atoms, preferably C16 and C18. In particular, the preferred conditions provide for a C16 fatty acid triglyceride content comprised between 35 and 55% and C18 between 45 and 60% of the total fatty acid content. The technique for applying the second coating layer is similar to the one used for the first one.

The total amount of coating applied is between 15 and 65% and preferably between 30 and 60% of the final weight of the granules or microparticles, said quantity being distributed between the first and second coating layers in a ratio comprised between 1:2.5 and 1:0.5.

A particular characteristic of the present invention is that it has been found surprisingly that the ability to control effectively the release, and consequently reduce the rumen degradation, of active substances which contain a cationic or anionic chemical function is determined by the synergistic action of two phenomena: an interaction between the active substance and the other component of the core; and the barrier effect of the double fat layer. Considered individually, the two phenomena are unable to control effectively the release of the active substance.

The ability of the silicates cited in the present invention to adsorb in water substances which have a cationic function in their chemical structure is in fact known (F. S. Grazy et al., *Pharmazie* (1984), 39, 821-3). However, this phenomenon alone is not sufficient to control effectively the release of substance from the microparticles, and likewise adequate control of the release rate of active substances (in particular those characterized by high water solubility) is not achieved by applying a double coating as described above to cores constituted by a supporting material which is unable to give rise to said interaction or which causes a too bland interaction. The type of silicate and the amount to be used are a significant aspect which characterizes the present invention in relation to what is disclosed in the patents cited above.

Another specific characteristic of the present invention is constituted by the presence of a coating around the core that contains the active substance, which is constituted by two layers. Differently from patent applications US Patent Publication No. 2005/0019413 and US Patent Publication No. 2006/0067984, the coating layer constituted by the material having the highest melting point is in direct contact with the core, while the layer constituted by the material having the lowest melting point is arranged on the outside of the granule or microparticle. This is an unquestionable advantage in terms of production method, since it allows to apply the two layers sequentially, preventing the layer in contact with the core from being damaged by even partial melting during the application of the second layer.

By way of non-limiting demonstration, examples related to the preparations and characteristics of the invention are cited hereafter.

Example 1

700 g of bentonite (Laviosa, Livorno, IT) were mixed with 1100 g of choline chloride crystals (Amik, Milano, IT) and 16 ml of purified water in the chamber of a rotary granulating machine of the RotoJ type (Zanchetta, Lucca, IT), applying a mixing speed of 200 rpm for 1 hour in order to facilitate adsorption of the choline on the bentonite. A vacuum drying step (chamber pressure 0.2 bar) was then performed with a chamber temperature of 40° C. at 100 rpm.

The resulting granules were then sorted with a screen having a 2.8-mm mesh pitch in order to eliminate any agglomerations of excessive size. Said granules represent the cores subsequently subjected to coating.

11.4 g of said granules were rolled in a drum mixer with a volume of 1 l, heated to the temperature of 65° C. with 4.3 g of a powder of a vegetable fat, constituted by a mixture of triglycerides which had the following percentage composition in fatty acid residues: C14, 1; C16, 15; C18, 83; C18', 0.8; C20, 0.4 (Eulip, Parma, IT). The drum mixer was made to roll and heated to said temperature until a layer of fat was distributed completely over the granules. After cooling, the resulting coated granules received the addition of 4.3 g of a powder of a vegetable fat, constituted by a mixture of triglycerides having the following percentage composition in fatty acid residues: C14, 1; C16, 45; C18, 53; C18', 0.5; C20, 04 (Eulip, Parma, IT). The drum mixer was made to roll and heated to the temperature of 59° C. until a layer of fat was distributed completely over the granules. Cooling caused the complete solidification of the second layer of fat.

Comparison Example 2

Granules coated according to the method described in Example 1 were prepared by way of comparison, using micronized silica (Degussa A G, Frankfurt am Main, Germany) instead of bentonite to form the core subsequently coated as described above.

Comparison Example 3

Granules coated according to the method described in Example 1 were prepared by way of comparison by using corn cob instead of bentonite to form the core subsequently coated as described above.

Comparison Example 4

Uncoated granules obtained according to the method described in Example 1 as regards core preparation were prepared by way of comparison.

Example 5

650 g of sodium calcium bentonite (Dal Cin, Milan, IT) were mixed with 44 g of microcrystalline cellulose (FMC, Philadelphia, USA) at 100 rpm in the chamber of a rotary granulating machine of the RotoJ type (Zanchetta, Lucca, IT). 960 g of choline chloride crystals (Amik, Milano, IT) and 20 ml of purified water were then added, applying a mixing speed of 200 rpm for 1 hour to facilitate adsorption of the choline on the bentonite. Subsequently, a step of vacuum drying was performed (chamber pressure 0.2 bars) with a chamber temperature of 50° C. at 100 rpm.

The granules thus obtained were sorted with a screen having a 3.5 mm mesh pitch in order to eliminate any agglomerations of excessive size.

13 g of said granules were rolled in a drum mixer having a volume of 1 l, heated to 65° C. with 2 g of a powder of a vegetable fat constituted by a mixture of triglycerides having the following percentage composition in terms of fatty acid residues: C14, 1; C16, 15; C18, 83; C18', 0.8; C20, 0.4 (Eulip, Parma, IT). The drum mixer was made to roll and heated to said temperature until a layer of fat was distributed completely over the granules. After cooling, the coated granules thus obtained received the addition of 5 g of a powder of a vegetable fat constituted by a mixture of triglycerides having the following percentage composition in fatty acid residues: C14, 1; C16, 45; C18, 53; C18', 0.5; C20, 0.4 (Eulip, Parma, IT). The drum mixer was made to roll and heated to 59° C. until a layer of fat was distributed completely over the granules. Cooling produced complete solidification of the second layer of fat.

Example 6

The coated granules prepared as described in Examples 1-5 (500 mg) were subjected to a test to determine the release rate of the choline chloride by using a paddle dissolver which turned at 100 rpm (FU XI). 1 l of phosphate buffer at pH 7.4 (FU IX), controlled by thermostat to the temperature of 40° C., was used as a dissolving medium. The quantity of choline chloride released in the various time intervals over 24 hours was determined by measuring its concentration in the dissolving medium by way of a previously validated HPLC method.

By way of comparison, two commercially available products, manufactured respectively by the Balchem company (Reashure Choline) and by the company Ascor Chimici (Sta-Chol) were also tested.

The results obtained are given in Table 1 as a percentage of choline chloride released after 1, 3, 5, 7 and 24 hours.

TABLE 1

| Product | Percentage of released choline chloride | | | | |
|---|---|---|---|---|---|
| | 1 hour | 3 hours | 5 hours | 7 hours | 24 hours |
| Example 1 | 0.75 | 4.3 | 7.4 | 10 | 27 |
| Example 2 | 34 | 56 | 61 | 73 | 100 |
| Example 3 | 2.3 | 9.3 | 16.2 | 24.5 | 67.4 |
| Example 4 | 100 | 100 | 100 | 100 | 100 |
| Example 5 | 0 | 0 | 0 | 0 | 7 |
| Balchem | 13.2 | 23 | 26 | 27 | 34.7 |
| Ascor Chimici | 36.4 | 55.8 | 70.3 | 77 | 100 |

It is noted that the product formulated as described in Example 1 has an optimum release over 24 hours. The product formulated as described in Example 5 is even more capable of controlling the release of the active substance, ensuring prolonged rumen protection.

As regards the commercial products, they release choline chloride at a higher rate than the formulations of Examples 1 and 5.

As regards the formulation described in Example 2, it is noted that the replacement of bentonite with silica determines a substantial loss of the ability to control release, and the same occurs for the formulation described in Example 3 by replacing the bentonite with corn cob. Finally, the use of bentonite alone, without the double fat coating (formulation described in Example 4), leads to immediate release of all the choline chloride.

Example 7

15.5 g of bentonite (Laviosa) were mixed in a mortar with 24.5 g of lysine hydrochloride crystals (DSM, Milano, IT) and mixed with 2 ml of purified water. Drying in an air circulation oven at 40° C. was then performed for 1 hour. The resulting granules were sorted with a screen having a mesh pitch of 2.8 mm in order to eliminate any agglomerations of excessive size. Said granules constitute the cores which were subsequently subjected to coating in the manner and with the materials described in Example 1.

A test was conducted on the produced granules to determine the release rate of lysine hydrochloride in the manner described in Example 6. The amount of lysine hydrochloride at the various tune intervals was determined by measuring its concentration in the dissolving medium by means of a chromatographic method.

The amount of released lysine hydrochloride expressed as a percentage of the dose that is present in the granules is given in Table 2

TABLE 2

| | Percentage of released lysine hydrochloride | | | |
|---|---|---|---|---|
| | 0.5 hours | 3 hours | 7 hours | 24 hours |
| Example 7 | 4.6 | 10 | 11.9 | 17.2 |

Good control in the release of lysine hydrochloride over 24 hours is observed, such as to ensure prolonged rumen protection.

Example 8

20 g of bentonite (Laviosa, Livorno, IT) were mixed in a mortar with 22 g of calcium chloride crystals (Solvay, Rosignano, IT) and mixed with 2 ml of purified water. A step of drying in an oven with air circulation at 40° C. for 1 hour was then performed.

The resulting granules were sorted with a screen having a mesh pitch of 2.8 mm in order to eliminate any agglomerations of excessive size. Said granules represent the cores which were subsequently subjected to coating in the manner and with the materials described in Example 1.

A test was conducted on the produced granules to determine the release rate of the calcium chloride in the manner described in Example 6. The amount of $CaCl_2$ at the various time intervals was determined by measuring its concentration in the dissolving medium by colorimetry (Calcium-Test, Merck KGaA, Darmstadt, Germany).

The amount of released $CaCl_2$ expressed as a percentage of the dose that is present in the granules is given in Table 3.

TABLE 3

| | Percentage of released $CaCl_2$ | | | | |
|---|---|---|---|---|---|
| Product | 1 hour | 3 hours | 5 hours | 7 hours | 24 hours |
| Example 8 | 6.4 | 19.5 | 28.8 | 41.7 | 85 |

It is noted a very good control in the calcium chloride release especially in the first hours.

Example 9

The granules produced in the manner described in Example 1 were subjected to a stability test according to ICH teachings (25° C.; 60% RH).

After 1, 3 and 6 months, the granules were subjected to a dissolution test as described in Example 6. The obtained results are given in FIG. 1.

The results show that over 6 months the formulation described in Example 1 maintains a good ability to control release, indicating good stability of the product.

Example 10

40 g of bentonite AG/1 W (Dal Cin, Milano, IT) were mixed in a mortar with a solution of 50 g of citric acid (UNIVAR, Milano, IT) dissolved in 15 ml of purified hot water. Drying in an air circulation oven at 40° C. was then performed for 1 hour.

The resulting granules were sorted with a screen having a mesh pitch of 2.8 mm in order to eliminate any agglomerations of excessive size. Said granules constitute the cores which were subsequently subjected to coating in the manner and with the materials described in Example 1.

A test was conducted on the produced granules to determine the release rate of citric acid in the manner described in Example 6. The amount of citric acid at the various time intervals was determined by measuring its concentration in the dissolving medium by means of a previously validated HPLC method. The amount of released citric acid expressed as a percentage of the dose that is present in the granules is given in Table 4.

TABLE 4

| | Percentage of released citric acid | | | |
|---|---|---|---|---|
| | 0.5 hours | 3 hours | 7 hours | 24 hours |
| Example 10 | 0 | 0 | 6.4 | 29.9 |

Very good control in the release of citric acid over 24 hours is observed, such as to ensure prolonged rumen protection.

The disclosures in Italian Patent Application No. MI2006A001583 from which this application claims priority are incorporated herein by reference.

The invention claimed is:

1. A system for the controlled release of one or more physiologically or pharmacologically active substances, comprising compositions in the form of microparticles or granules, particularly for use in the zootechnical and/or veterinary field, comprising:
a core which contains one or more active ingredients selected from substances having a pharmacological action, food supplements, or diagnostic media, said one or more substances being characterized by the presence, within their chemical structure, of a cationic function or of an anionic function or of a function which is neutral but can be easily ionized, obtaining a net charge, mixed or adsorbed with a hydrated silicate selected from the group consisting of magnesium, aluminum, calcium and sodium hydrated silicates in an amount between 20 and 80 percent by weight of the core, which chemically interacts with the one or more active ingredients and are capable of absorbing water and causing reversible swelling, said core being coated by a double fatty layer constituted by a first inner layer, which comprises a fat having melting point from between about 63 to about 90° C. and is in contact with the core, and a second outer layer, which comprises a fat having a lower melting point than the fat in the first layer; and wherein the silicate is selected from the group constituted by smectite, montmorillonite or bentonite.

2. The system according to claim 1, characterized in that the silicates comprise between about 35 and 55 percent by weight of the core.

3. The system according to claim 1, characterized in that said one or more substances are selected from the group constituted by choline and its salts, particularly choline chloride, betaine, betaine hydrochloride, methionine hydrochloride, arginine, arginine hydrochloride, niacinamide, niacinamide hydrochloride, carnitine hydrochloride, lysine hydrochloride, thiamine hydrochloride, thiamine mononitrate, pyridoxine hydrochloride, calcium chloride, calcium sulfate, streptomycin, colistin sulfate, glucosamine, glucosamine sulfate, tiamulin fumarate, neomycin and salts thereof, particularly neomycin sulfate; citric acid, malic acid, fumaric acid, lactic acid, ascorbic acid, nicotinic acid.

4. The system according to claim 1, characterized in that said core further comprises excipients which are capable of improving the formation of the granules or microgranules.

5. The system according to claim 4, characterized in that said excipients are selected from the group constituted by microcrystalline cellulose, chitosan, polyvinylpyrrolidone, starch and calcium phosphate.

6. The system according to claim 4, characterized in that said excipients are present in a quantity comprised between 1 and 15% by weight with respect to the weight of said silicate.

7. The system according to claim 1, characterized in that said one or more substances are present in a quantity comprised between 80 and 20 parts by weight, with reference to the weight of the core.

8. The system according to claim 1, characterized in that said first layer comprises a vegetable fat with a melting point comprised between 63 and 90° C.

9. The system according to claim 8, wherein said fat comprises a mixture of partially hydrogenated fatty acid triglycerides or a mixture of free fatty acids, with a chain of 14 to 20 carbon atoms.

10. The system according to claim 9, characterized in that said mixture comprises C16 fatty acid triglycerides between 10 and 30% by weight and C18 fatty acid triglycerides between 65 and 90% by weight with reference to the total content of fatty acids.

11. The system according to claim 1, characterized in that said second layer comprises a vegetable fat which has a melting point comprised between 59 and 62° C.

12. The system according to claim 11, characterized in that said fat comprises a mixture of partially hydrogenated fatty acid triglycerides, or a mixture of free fatty acids, with a chain of 14 to 20 carbon atoms.

13. The system according to claim 12, characterized in that said mixture contains C16 fatty acid triglycerides between 35 and 55% and C18 fatty acid triglycerides between 45 and 60% with reference to the total fatty acid content.

14. The system according to claim 1, characterized in that said double fatty layer constitutes 15 to 65% by weight, with reference to the total weight of said granules or microparticles.

15. The system according to claim 14, characterized in that said first and second layer are comprised in a weight ratio between 1:2.5 and 1:0.5.

16. The system according to claim 4, characterized in that said excipients are comprised in said mixture in a percentage between 2 and 20% by weight.

17. The system according to claim 1, characterized in that said microparticles or granules have an average volume diameter between 0.1 μm and 5.000 μm.

18. A method for preparing a system, comprising the following steps: preparing a mixture of powders which comprises one or more physiologically or pharmacologically active substances and a hydrated silicate selected from the group consisting of magnesium, aluminum, calcium and sodium hydrated silicates in an amount between 20 and 80 percent by weight of the mixture which chemically interacts with the one or more active substances and are capable of absorbing water and causing reversible swelling; and wherein the silicate is selected from the group constituted by smectite, montmorillonite or bentonite, and optionally one or more excipients capable of improving the formation of granules or microgranules, forming microgranules or granules from said mixture by adding water in an amount sufficient to achieve agglomeration but not a cohesive mix, drying, if necessary, said granules or microgranules, coating said granules or microgranules with a first layer comprising a first fat having a melting point from between about 63 and about 90° C., and coating said granules coated with a first layer with a second layer comprising a second which has a lower melting point than said first fat.

19. The method according to claim 18, characterized in that said silicate is present in a quantity comprised between 20 and 80% by weight, of said mixture.

20. The method according to claim 18, characterized in that said excipients are comprised in said mixture in a percentage between 2 and 20% by weight with reference to the weight of the mixture.

21. The method according to claim 18, characterized in that water is added in a quantity comprised between 5 and 50% with reference to the weight of the mixture of powders.

22. A method for preparing a system according to claim 1, comprising the steps of: forming granules or microgranules of powder of said hydrated silicate, spraying or mixing said granules or microgranules with an aqueous solution which comprises said one or more substances, optionally drying said granules or microgranules, coating said granules or microgranules with a first layer comprising a first fat, and coating said granules coated with a first layer with a second layer comprising a fat which has a lower melting point than said first fat.

23. The method according to claim 22, characterized in that said solution has a concentration of said one or more substances comprised between 0.05 and 0.95 g/ml.

24. The method according to claim 18, characterized in that said excipients are comprised in a percentage between 1 and 15% by weight with reference to the weight of the silicate.

25. The method according to claim 18, characterized in that the formation of granules or microgranules occurs by a method selected among extrusion-spheronization, fluid-bed granulation, rotating plate granulation, high-speed granulation and wet granulation.

26. The method according to claim 18, characterized in that the coating of a fat occurs after melting said fat, by means of a method selected from fluid-bed or spray congealing, or by coating in a drum mixer.

27. The method according to claim 18, characterized in that the preparation of said microparticles or granules occurs without using organic solvents.

28. A controlled release composition, comprising: (a) a core obtained from ingredients comprising (i) one or more active substances selected from substances having a pharmacological action, food supplements, or diagnostic media, wherein said one or more substances comprise a cationic function, an anionic function, or a neutral function that is ionizable in aqueous media; and (ii) a hydrated silicate in an amount between 20 and 80 percent by weight of the core which chemically interacts with the one or more active ingredients and are capable of absorbing water and causing reversible swelling; and wherein the silicate is selected from the group constituted by smectite, montmorillonite or bentonite; (b) a first, inner coating layer comprising a first fat; and (c) a second, outer coating comprising a second fat, wherein the second fat has a lower melting point than the first fat.

29. A method of making a controlled release composition, comprising the steps of: (a) forming a particle obtained from ingredients comprising (i) one or more active substances selected from substances having a pharmacological action, food supplements, or diagnostic media, wherein said one or more substances comprise a cationic function, an anionic function, or a neutral function that is ionizable in aqueous media; and (ii) a hydrated silicate in an amount between 20 and 80 percent by weight of the particle which chemically interacts with the one or more active substances and are capable of absorbing water and causing reversible swelling; wherein the silicate is selected from the group constituted by smectite, montmorillonite or bentonite; (b) coating the particle with a first coating comprising a first fat; and (c) coating the coated particle of step (b) with a second coating comprising a second fat, wherein the second fat has a lower melting point than the first fat.

30. A controlled release composition, comprising: (a) a core obtained from ingredients comprising (i) one or more active substances selected from substances having a pharmacological action, food supplements, or diagnostic media, wherein said one or more substances comprise a cationic function, an anionic function, or a neutral function that is ionizable in aqueous media; and (ii) a clay selected from the group consisting of smectite, a montmorillonite, and a bentonite in an amount between 20 and 80 percent by weight of the core which chemically interacts with the one or more active substances and are capable of absorbing water and causing reversible swelling; (b) a first, inner coating layer comprising a first fat; and (c) a second, outer coating comprising a second fat, wherein the second fat has a lower melting point than the first fat.

31. A method of making a controlled release composition, comprising the steps of: (a) forming a particle obtained from ingredients comprising (i) one or more active substances selected from substances having a pharmacological action, food supplements, or diagnostic media, wherein said one or more substances comprise a cationic function, an anionic function, or a neutral function that is ionizable in aqueous media; and (ii) a clay selected from the group consisting of smectite, a montmorillonite and a bentonite in an amount between 20 and 80 percent by weight of the particle which chemically interacts with the one or more active substances and are capable of absorbing water and causing reversible swelling; (b) coating the particle with a first coating comprising a first fat; and (c) coating the coated particle of step (b) with a second coating comprising a second fat, wherein the second fat has a lower melting point than the first fat.

* * * * *